United States Patent [19]

Takatsuna et al.

[11] Patent Number: 4,897,501

[45] Date of Patent: Jan. 30, 1990

[54] PROCESS FOR PREPARING AMINOPROPYL ALKOXY SILANES

[75] Inventors: Kazutoshi Takatsuna, Saitama, Japan; Mamoru Tachikawa, Midland, Mich.; Kouji Shiozawa; Nobukazu Okamoto, both of Saitama, Japan; Yoshiharu Okumura, Tokyo, Japan

[73] Assignee: Toa Nenryo Kogyo Kabushiki Kaisha, Tokyo, Japan

[21] Appl. No.: 226,086

[22] Filed: Jul. 29, 1988

[30] Foreign Application Priority Data

Jul. 31, 1987 [JP] Japan ................................. 62-192263

[51] Int. Cl.$^4$ ................................................ C07F 7/10
[52] U.S. Cl. ..................................... 556/413; 556/424
[58] Field of Search ................................. 556/413, 424

[56] References Cited

U.S. PATENT DOCUMENTS 4,481,364 11/1984 Chu et al. .............................. 556/413
4,556,722 12/1985 Quirk et al. .......................... 556/413

*Primary Examiner*—Paul F. Shaver
*Attorney, Agent, or Firm*—Wenderoth, Lind & Ponack

[57] ABSTRACT

In a process for preparing aminopropyl alkoxy silanes comprising reacting an allylamine with a hydro-alkoxy silane in the presence of a rhodium catalyst, the improvement which comprises use of a rhodium phosphide or its oligomer as said rhodium catalyst. By this process the desired gamma-isomer can be prepared in a high selectivity and yield within a short reaction time.

4 Claims, No Drawings

PROCESS FOR PREPARING AMINOPROPYL ALKOXY SILANES

TECHNICAL FIELD OF THE INVENTION

The present invention relates to a process for preparing aminopropyl alkoxy silanes. More particularly, it relates to a process for preparing aminopropyl alkoxy silanes wherein an allylamine is reacted with a hydro-alkoxy silane using as a catalyst a rhodium phosphide complex. As known in the art, the aminopropyl alkoxy silanes are useful as silane coupling agents.

BACKGROUND OF THE INVENTION

Silane coupling agents are compounds having in their molecule an organic functional group and a hydrolyzable group reactive with inorganic materials. Since the silane coupling agents are, due to their functional groups, capable of chemically bonding an organic polymer with an organic material, such as silica, thereby remarkably increasing the mechanical strength of the organic polymer, demand for them is increasing as an indispensable material in the development of ultrafashionable composite materials.

Gamma-aminopropyl alkoxy silanes are used in the art as the silane coupling agent, and it is known that they can be prepared by hydrosililation of an allylamine, which may be substituted on the nitrogen atom, with a hydro-alkoxy silane.

For example, Japanese Patent Laid-open Publication No. 60-81189 discloses a process for the preparation of aminopropyl alkoxy silanes, which comprises reacting an allylamine with a hydro-alkoxy silane using a platinum catalyst, such as chloroplatinic acid, in the presence of a promoter, such as anhydrous sodium carbonate. However, the reaction of an allylamine with a hydro-alkoxy silane in the presence of a platinum catalyst, such as chloroplatinic acid, inevitably produces the corresponding beta-aminopropyl alkoxy silane which may be referred to herein as the beta-isomer in addition to the desired gamma-aminopropyl alkoxy silane, which may be referred to herein as the gamma-isomer, normally with a ratio of the gamma-isomer to the beta-isomer of from 4 to 6, posing a problem in that the selectivity of the desired gamma-isomer is not satisfactorily high. An attempt to separate the gamma-isomer from the beta-isomer is not attractive, since it requires a distillation tower having a considerable number of distillation plates.

Japanese Patent Laid-open Publication No. 61-229885 discloses a process for the preparation of aminopropyl alkoxy silanes by reacting an allylamine with a hydro-alkoxy silane in the presence of a catalyst comprising rhodium-organic tertiary phosphine complex and optionally triphenylphosphine. By this process gamma-aminopropyl alkoxy silanes can be prepared in a high selectivity. The process is disadvantageous, however, in that a prolonged reaction time is required to achieve a high conversion. Further, an excessive amount of triphenylphosphine must be used to achieve a high selectivity of the gamma-isomer, leading to a possible contamination of the finally distilled product by the triphenylphosphine.

OBJECT OF THE INVENTION

The invention is to solve the problems involved in the prior art and an object of the invention is to provide a process for preparing aminopropyl alkoxy silanes from a hydro-alkoxy silane and an allylamine having at least one active hydrogen atom attached to the amine nitrogen atom, in a high selectivity and yield within a shortened reaction time.

SUMMARY OF THE INVENTION

It has now been found that if the hydrosililation of an allylamine with a hydro-alkoxy silane is carried out in the presence of a special rhodium phosphide or its oligomer, the reaction proceeds quickly and provides the desired gamma-isomer in a high selectivity and yield.

Thus, a process of preparing aminopropyl alkoxy silanes according to the invention comprises reacting an allylamine of the formula [I]

wherein $R_1$ and $R_2$ each represents hydrogen, alkyl having from 1 to 10 carbon atoms, alkenyl having from 2 to 10 carbon atoms, phenyl, substituted phenyl, $-CH_2CH_2NHCH_2CH_2NH_2$ or $-CH_2CH_2NH_2$, and $R_3$ is hydrogen or alkyl having from 1 to 6 carbon atoms with a hydro-alkoxy silane of the formula [II]

wherein $R_4$, $R_5$ and $R_6$, each represents alkyl or alkoxy, at least one of $R_4$, $R_5$ and $R_6$, being alkoxy, in the presence of a rhodium phosphide of the general formula

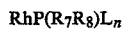

wherein $R_7$ and $R_8$ each is alkyl having from 1 to 20 carbon atoms, alkoxy having from 1 to 20 carbon atoms, aryl having from 6 to 20 carbon atoms or aryloxy, having from 6 to 20 carbon atoms, L is olefin, diolefin, aromatic amine, nitrile, isonitrile or carbonyl and n is from 1 to 2, or its oligomer, as a catalyst.

DETAILED DESCRIPTION OF THE INVENTION

A process for preparing aminopropyl alkoxy silanes according to the invention will be fully described hereinafter.

Allylamines

Allylamines as represented by the formula [I], can be used in the process for preparing aminopropyl alkoxy silanes according to the invention.

Examples of such allylamines include, for example, allylamine, N-methylallylamine, N-ethylallylamine, N,N-dimethylallylamine, N,N-diethylallylamine, 2-methylallylamine, diallylamine and allylethylenediamine.

Hydro-alkoxy silanes

Hydro-alkoxy silanes having from 1 to 3 alkoxy groups attached to the silicon atom, as represented by the formula [II] can be used in the process for preparing aminopropyl alkoxy silanes according to the invention.

Examples of hydro-alkoxy silanes of the formula [II] include, for example, triethoxy silane, trimethoxy silane, tripropoxy silane, tributoxy silane, methyl dimethoxy silane, ethyl dimethoxy silane, methyl diethoxy silane, dimethyl methoxy silane, trioctyloxy silane, methyl dioctyloxy silane and dimethyloctyloxy silane.

Rhodium phosphides

When an allylamine as described above is reacted with a hydro-alkoxy silane as described above according to the invention, use is made, as a catalyst, of a rhodium phosphide of the general formula $RhP(R_7R_8)L_n$ or its oligomer. In the formula above, $R_7$ and $R_8$ each is alkyl having from 1 to 20 carbon atoms, alkoxy having from 1 to 20 carbon atoms, aryl having from 6 to 20 carbon atoms or aryloxy, having from 6 to 20 carbon atoms, L is olefin, diolefin, aromatic amine, nitrile, isonitrile or carbonyl and n is from 1 to 2.

Examples of the ligand $P(R_7R_8)$ include, for example, dimethyl phosphide, dibutyl phosphide, di-t-butyl phosphide, diphenyl phosphide, ditolyl phosphide, phenyl ethyl phosphide, dibutoxy phosphide and diphenoxy phosphide.

Examples of the ligand L include, for example, monolefins such as ethylene, propylene and cyclooctene; conjugated dienes such as 1,3-butadiene, 1,3-pentadiene and 1,3-cyclohexadiene; non-conjugated dienes such as 1,5-cyclooctadiene, norbornadiene and 1,4-pentadiene; aromatic amines such as pyridine, dipyridyl and ortho-phenanthroline; nitrile, isonitrile and carbonyl.

These rhodium phosphides are generally unstable in the form of monomer, and stably exist in the form of oligomer such as dimer and trimer. However, they might be existing in the form of monomer under the reaction conditions.

Examples of oligomers of rhodium phosphides include:

[Rh(CO)$_2$P Ph$_2$]$_m$,
[Rh$_3$(P Ph$_2$)$_3$(CO)$_5$],
[Rh$_4$(CO)$_5$(P Ph$_2$)$_5$],
[Rh(CO)$_2$P(t-Bu)$_2$]$_m$,
[Rh(COD)P Ph$_2$]$_m$,
[Rh(COD)P Me Ph]$_m$,
[Rh(C$_2$H$_4$)$_2$P Ph$_2$]$_m$,
[Rh(TFB)P Ph$_2$]$_m$,
[Rh(1,5-C$_6$H$_{10}$)P Ph$_2$]$_m$,
[Rh(NBD)P Et$_2$]$_m$,
[Rh(Dipyridyl)P Me$_2$]$_m$,
[Rh(Me CN)$_2$P Ph$_2$]$_m$, and
[Rh(Me NC)$_2$P Me Bu]$_m$ wherein Ph is phenyl, COD is cyclooctadiene, Me is methyl, TFB is tetrafluorobenzobarrelene, NBD is norbornadiene, Et is ethyl, Bu is butyl and m is 2, 3 or 4.

The rhodium phosphide may be separately prepared and the catalyst so prepared may be added to the reaction system, or it may be formed in the reaction system and the rhodium phosphide so formed in situ may be used as the catalyst.

Reaction conditions

The allylamine and hydro-alkoxy silane are preferably used in such amounts that a ratio of the allylamine to the hydro-alkoxy silane by mole is within the range from about 1.3:1 to about 1:1.3.

The reaction may be carried out under atmospheric or elevated pressure. The reaction is normally carried out at a temperature of at lest 50° C., preferably from about 50° C. to about 250° C. If a reaction temperature substantially below 50° C. is used, the desired gamma-isomer will be formed in small amounts. Whereas, as the reaction temperature approaches and exceeds about 250° C., increasing amounts of the beta-isomer tend to be formed, undesirably lowering the selectivity of the gamma-isomer. Preferred reaction temperatures are from about 100° C. to about 200° C.

While the rhodium phosphide or its oligomer may be used in an excess amount, it is sufficient for it to be present in the reaction system in an amount on the order of from $10^{-6}$ to $10^{-3}$ mole per mole of the allylamine, on a rhodium basis.

In carrying out the reaction, solvents may or may not be used. When solvents are used, generally, hydrocarbon solvents such as toluene, xylene, heptane and dodecane, and ethers such as 1,4-dioxane and tetrahydrofuran are preferred.

While the reaction time greatly depends upon the reaction temperature used, it may normally be within the range between about 0.5 and about 2.0 hours.

When an allylamine is reacted with a hydro-alkoxy silane in the presence of a rhodium phosphide complex or its oligomer in accordance with the invention, we have found as shown in the following Examples, that the corresponding gamma-aminopropyl alkoxy silane can be produced in a high selectivity. For example, the gamma-isomer can be produced with a gamma/beta ratio as high as 80 or more. Further, the reaction rapidly proceeds, and thus, the gamma-isomer can be obtained in a yield as high as up to 80%.

In contrast, if an allylamine is reacted with a hydro-alkoxy silane, using a chloroplatinic acid catalyst, the yield of the gamma-isomer is on the order of 40–50%, with a gamma/beta ratio of about 4. Further, if an allylamine is reacted with a hydro-alkoxy silane, using rhodium hydride carbonyl tris(triphenylphosphine) complex as a catalyst, the gamma-isomer with a high gamma/beta ratio can only be obtained at the cost of a prolonged reaction time, e.g., 6 hours, owing to a slow reaction velocity.

While the invention is illustrated by the following examples, the invention is not limited thereto.

EXAMPLE 1

A three-neck flask equipped with a reflux condenser, stirring rod and thermometer was charged with 14 grams of allylamine (0.25 mole), 41 grams of triethoxy silane (0.25 mole), 20 ml. of p-xylene and 0.1% by mole (calculated as rhodium), per mole of triethoxysilane, of [Rh($\mu$-P Ph$_2$) (COD)]$_2$, that is [rhodium($\mu$-diphenyl phosphide) (1,5-cyclooctadiene) dimer], and heated on an oil bath maintained at a temperature of 110° C. About 1 hour after the beginning of the reaction, the reaction temperature reached 110° C. At the end of the period the reaction mixture was subjected to gas chromatography analysis. It was found that gamma-aminopropyl triethoxy silane was obtained in a yield of 81% on an allylamine basis, while the yield of beta-aminopropyl triethoxy silane was 0.7% on a triethoxy silane basis.

EXAMPLE 2

Example 1 was repeated except that the 41 grams of triethoxy silane was replaced with 30.6 grams of trimethoxy silane (0.25 mole) and toluene was used as a solvent instead of p-xylene, with other conditions remaining the same. After the completion of the reaction, the reaction mixture was subjected to gas chromatography analysis. It was found that gamma-aminopropyl trimethoxy silane was obtained in a yield of 70% on an allylamine basis, while the yield of beta-amminopropyl trimethoxy silane was 0.9% on an a trimethoxy silane basis.

EXAMPLE 3

Example 1 was repeated except that the allylamine was replaced with 25 grams of allylethylenediamine (0.25 mole), and n-dodecane was used as a solvent instead of p-xylene, with other conditions remaining the same. After the completion of the reaction the reaction mixture was subjected to gas chromatography analysis. It was found that the gamma-isomerk (gamma-ethylenediaminopropyl triethoxy silane) was obtained in a yield of 67% on a triethoxy silane basis, while the yield of the beta-isomer was 0.8% on a triethoxy silane basis.

EXAMPLE 4

The reaction of allylamine with triethoxy silane as in Example 1 was repeated, except that the amount of the catalyst was reduced to 0.02% by mole (calculated as rhodium) per mole of triethoxysilane and 20 ml of tetrahydrofuran was used as an additional solvent, with other conditions remaining the same. After the completion of the reaction, the reaction mixture was subjected to gas chromatography analysis. It was found that the gamma-isomer was obtained in a yield of 92% on a triethoxy silane basis, while the yield of the beta-isomer was 1.1% on a triethoxy silane basis.

EXAMPLE 5

To a solution of 0.48 gram (2.5 millimoles) of [rhodium dicarbonyl) (μ-chloro)]dimer that is [Rh(CO)$_2$Cl]$_2$ in 10 ml of tetrahydrofuran was added dropwise a separately prepared solution of about 3 millimoles of diphenyl phosphide lithium (Ph$_2$P Li) in tetrahydrofuran, and the mixture was stirred for a period of about 3 hours. From the mixture tetrahydrofuran was removed and the solid obtained was extracted with hexane. From the resulting hexane solution hexane was evaporated off, leaving a blackish green solid which was an oligomer of rhodium (μ-diphenyl) phosphide dicarbonyl.

Example 1 was repeated except that the so prepared oligomer of rhodium (μ-diphenyl) phosphide dicarbonyl, was used as a catalyst instead of the [Rh(μ-P Ph$_2$)(COD)]$_2$ of Example 1, with other conditions remaining the samme. After the completion of the reaction, the reaction mixture was subjected to gas chromatography analysis. It was found that the gamma-isomer was obtained in a yield of 81% on a triethoxy silane basis, while the yield of the beta-isomer was 0.9% on a triethoxy silane basis.

COMPARATIVE EXAMPLE 1

A four-neck flask equipped with a reflux condenser, dropping funnel, stirring rod and thermometer was charged with 41 grams of triethoxy silane (0.25 mole) and a solution of chloroplatinic (IV) acid as a catalyst, in isopropyl alcohol in an amount to provide 2×10$^{-5}$ mole of platinum. To the mixture heated in an oil bath maintained at a temperature of 120° C., 14 grams of allylamine (0.25 mole) was dropwise added over one hour from the dropping funnel. The mixture was maintained at 120° C. for another period of 9 hours. At the end of the period the reaction mixture was subjected to gas chromatography analysis. It was found that gamma-aminopropyl triethoxy silane was obtained in a yield of 44% on a triethoxy silane basis, while the yield of beta-aminopropyl triethoxy silane was 10% on a triethoxy silane basis.

COMPARATIVE EXAMPLE 2

A four-neck flask equipped with a reflux condenser, dropping funnel, stirring rod and thermometer was charged with 41 grams of triethoxy silane (0.25 mole), 0.12 gram of rhodium hydride carbonyltris(triphenylphosphine) as a catalyst and 1.4 grams of triphenyl phosphine. The mixture was heated to a temperature of 110° C. and 14 grams of allylamine (0.25 mole) was dropwise added over one hour from the dropping funnel. The mixture was maintained at 110° C. for a further hour. At the end of the period, it was revealed by gas chromatography that gamma-aminopropyl triethoxy silane was produced in a yield of 34% on an allylamine basis. The reaction mixture was maintained for further 4 hours. At the end of the period the yields of gamma- and beta-aminopropyl triethoxy silanes reached 71% and 6.9% on a triethoxy silane basis, respectively.

It can be seen from the foregoing that we have prepared gamma-aminopropyl alkoxy silanes in a high selectivity and yield within a short period of reaction time.

What is claimed is:

1. A process for preparing aminopropyl alkoxy silanes which comprises reacting an allylamine of the formula [I]

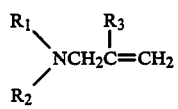

wherein R$_1$ and R$_2$ each represents hydrogen, alkyl having from 1 to 10 carbon atoms, alkenyl having from 2 to 10 carbon atoms, phenyl, substituted phenyl, —CH$_2$CH$_2$NHCH$_2$CH$_2$NH$_2$ or —CH$_2$CH$_2$NH$_2$, and R$_3$ is hydrogen or alkyl having from 1 to 6 carbon atoms with a hydro-alkoxy silane of the formula [II]

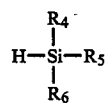

wherein R$_4$, R$_5$ and R$_6$, each represents alkyl or alkoxy, at least one of R$_4$, R$_5$ and R$_6$, being alkoxy in the presence of a rhodium phosphide of the general formula

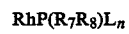

wherein R$_7$ and R$_8$ each is alkyl having from 1 to 20 carbon atoms, alkoxy having from 1 to 20 carbon atoms, aryl having from 6 to 20 carbon atoms or aryloxy having from 6 to 20 carbon atoms, L is olefin, diolefin, aromatic amine, nitrile, isonitrile or carbonyl and. n is from 1 to 2, or its oligomer, as a catalyst.

2. The process in accordance with claim 1 in which the catalyst is selected from [Rh(CO)$_2$P Ph$_2$]$_m$, [Rh$_3$(P Ph$_2$)$_3$(CO)$_5$], [Rh$_4$(CO)$_5$(P Ph$_2$)$_5$], [Rh(CO)$_2$P(t-Bu)$_2$]$_m$,

[Rh(COD)P Ph$_2$]$_m$, [Rh(COD) P Me Ph]$_m$, [Rh(C$_2$H$_4$)$_2$P Ph$_2$]$_m$, [Rh(TFB)P Ph$_2$]$_m$, [Rh(1,5-C$_6$H$_{10}$) P Ph$_2$]$_m$, [Rh(NBD)P Et$_2$]$_m$, [Rh(Dipyridyl)P Me$_2$]$_m$, [Rh(Me CN)$_2$P Ph$_2$]$_m$, and [Rh(Me NC)$_2$P Me Bu]$_m$ wherein Ph is phenyl, COD is cyclooctadiene, Me is methyl, TFB is tetrafluorobenzobarrelene, NBD is norbornadiene, Et is ethyl, Bu is butyl and m is 2, 3 or 4.

3. The process in accordance with claim 1 in which the allylamine is selected from allylamine, N-methylallylamine, N-ethylallylamine, N,N-dimethylallylamine, N,N-diethylallylamine, 2-methylallylamine, diallylamine and allylethylenediamine.

4. The process in accordance with claim 1 in which the hydro-alkoxy silane is selected from triethoxy silane, trimethoxy silane, tripropoxy silane, tributoxy silane, methyl dimethoxy silane, ethyl dimethoxy silane, methyl diethoxy silane, dimethyl methoxy silane, trioctyloxy silane, methyl dioctyloxy silane and dimethyl octyloxy silane.

* * * * *

UNITED STATES PATENT AND TRADEMARK OFFICE
CERTIFICATE OF CORRECTION

PATENT NO. : 4,897,501

DATED : January 30, 1990

INVENTOR(S) : Kazutoshi TAKATSUNA et al.

It is certified that error appears in the above-identified patent and that said Letters Patent is hereby corrected as shown below:

Column 1, line 20, change "organic" to --inorganic--.

Column 5, line 6, change "amminopropyl" to --aminopropyl--;

line 17, change "isomerk" to --isomer--;

line 53, change "samme" to --same--.

Signed and Sealed this

Fifth Day of October, 1993

Attest:

BRUCE LEHMAN

Attesting Officer

Commissioner of Patents and Trademarks